US00PP09564P

United States Patent [19]

Meilland

[11] Patent Number: Plant 9,564

[45] Date of Patent: May 28, 1996

[54] HYBRID TEA ROSE PLANT NAMED 'MEITOIFAR'

[75] Inventor: Alain A. Meilland, Antibes, France

[73] Assignee: The Conard-Pyle Company, West Grove, Pa.

[21] Appl. No.: 526,178

[22] Filed: Sep. 11, 1995

[51] Int. Cl.[6] ..... A01H 5/00

[52] U.S. Cl. ..... Plt./19

[58] Field of Search ..... Plt./11, 18, 19, Plt./20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive large double blossoms that are Bengal pink in coloration. Such blossoms are relatively stable in coloration, long-lasting, and commonly are borne in flushes. The petal drop characteristic is good. The plant exhibits a vigorous growth habit and exhibits very good disease resistance including a resistance to Marssonina disease. The new variety is particularly well suited for growing as attractive ornamentation in the landscape.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the artificial pollination of the 'Delset' variety (non-patented in the United States) and the 'Eden Rose' variety (U.S. Plant Pat. No. 1,149). The 'Delset' variety is marketed under the Versailles trademark. The male parent (i.e., the pollen parent) was the 'Kimono' variety (non-patented in the United States). The parentage of the new variety can be summarized as follows:

('Delset'×'Eden Rose')×'Kimono'.

The seeds resulting from the above pollination were sown and 120 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive large long-lasting Bengal Pink blossoms that exhibit a strong fragrance,
(b) exhibits a vigorous growth habit,
(c) exhibits very good disease resistance, and
(d) is particularly well suited for growing as attractive ornamentation in the landscape.

The pink blossoms coloration of the new variety is relatively stable upon the passage of time.

The new variety well meets the needs of the horticultural industry and is particularly well adapted for growing outdoors in parks and gardens.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meitoifar' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelii* understock and growing outdoors at Le Cannet des Maures, Var, France.

DETAILED DESCRIPTION

Figures 1, 2, 3, 4, 5, 6, 7, 8, 9, 10, 11, 12, 13, 14, 15:
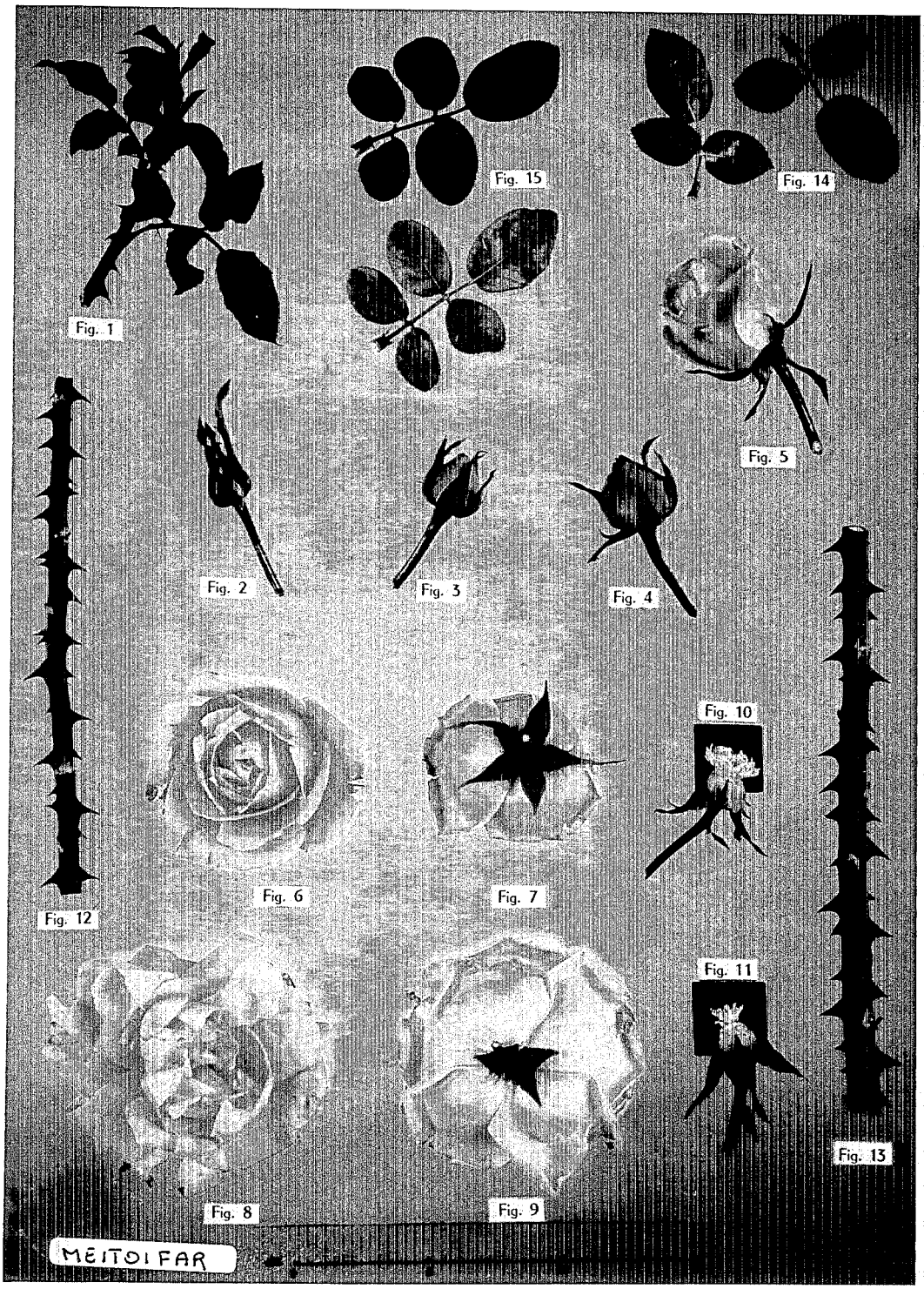
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — plan view — upper surface (right) and lower surface (left)
FIG. 15 illustrates specimens of leaves with five leaflets — plan view — under surface (top) and under surface (bottom).

The chart used in the identification of the colors is that of The Royal Horticultural Society (R.H.S. Colour Chart). Color terminology in common terms commonly precedes reference to the chart. The description is based on the observation during June of two year-old plants while budded on *Rosa froebelii* understock and growing outdoors at Le Cannet des Maures, Var, France.

Class: Hybrid Tea.

Plant:

Height.—Approximately 90 to 100 cm. on average at the end of the growing season.

*Habit.*—Bushy.

Branches:

*Color.*—Young stems: light green, Yellow-Green Group 146C. Adult wood: light green, Green Group 143C.

*Thorns.*—Size: medium. Quantity: numerous. Color: reddish in coloration on young stems and more pinkish in coloration on adult wood.

Leaves:

*Stipules.*—Adnate, pectinate, very wide and linear.

*Petioles.*—Upper surface: striped reddish on young foliage, and medium green on adult foliage with more or less glandular edges. Under surface: light green with a few prickles.

*Leaflets.*—Number; 3, 5, and 7 (most often). Shape: elliptic. Serration: simple and regular. Texture: leathery. General appearance: dense, and semi-dull foliage. Color (young foliage): Upper surface: medium green, Yellow-Green Group 146B, and more or less tinted with reddish brown. Under surface: light green, Yellow-Green Group 146C. Color (adult foliage): Upper surface: dark green, Green Group 137A. Under surface: light green, Green Group 139C.

Inflorescence:

*Number of flowers.*—Usually one flower per stem, and sometimes up to approximately 3 flowers per stem.

*Peduncle.*—Light green and widely maculated with reddish coloration. The length is approximately 4 to 6 cm. on average.

*Sepals.*—Upper surface: tomentose, and greenish in coloration. Under surface: medium green and more or less maculated with reddish coloration. The sepals may possess a few appendages (as illustrated).

Buds.—Shape: ovoid. Length: approximately 2.5 cm. on average. Size: medium. Color upon opening: Upper surface: dark Indian Pink, Red-Purple Group 58B. Under surface: dark Indian Pink, Red-Purple Group 58B.

*Flower.*—Shape: double and cup-shaped with a substantially flat center. Diameter: approximately 10 to 11 cm. on average. Color (when opening begins): Upper surface: dark Indian Pink, Red-Purple Group 58B. Under surface: dark Indian Pink, Red-Purple Group 58B. Color (when blooming): Upper surface: dark Indian Pink, Red-Purple Group 58B. Under surface: Bengal Pink, Red-Purple Group 57D. Color (at end of opening): Upper surface: dark Indian Pink, Red-Purple Group 58B. Under surface: Bengal Pink, Red-Purple Group 57D. Fragrance: strong. Lasting quality: very long. Petal shape: rounded to oval with a cuneate base. Petal number: approximately 50 to 65 on average. Petal drop: good. Stamen number: approximately 52 on average. Anthers: normal and golden yellow in coloration. Filaments: normal and sometimes mixed with very small petals. Pistils: approximately 58 on average. Stigmas: normal. Sytles: greenish in coloration. Receptacle: medium green in coloration, more or less tinted with reddish coloration, smooth, and in longitudinal section in the shape of a funnel.

Development:

*Vegetation.*—Vigorous.

*Blooming.*—Abundant and commonly in flushes.

*Resistance to diseases.*—Very good, and is very resistant to Marssonina disease.

I claim:

1. A new and distinct variety of Hybrid Tea rose plant characterized by the following combination of characteristics:

(a) forms in abundance attractive large long-lastiong Bengal Pink blossoms that exhibit a strong fragrance,
(b) exhibits a vigorous growth habit,
(c) exhibits very good disease resistance, and
(d) is particularly well suited for growing as attractive ornamentation in the landscape;

substantially as herein shown and described.

* * * * *

MEITOI FAR